(12) United States Patent
Al-Ahmed et al.

(10) Patent No.: US 9,862,675 B1
(45) Date of Patent: Jan. 9, 2018

(54) METHOD OF N-FORMYLATING AMINES WITH A PHOSPHONIC ANHYDRIDE

(71) Applicant: KING FAHD UNIVERSITY OF PETROLEUM AND MINERALS, Dhahran (SA)

(72) Inventors: Amir Al-Ahmed, Dhahran (SA); Arun M. Isloor, Mangalore (IN)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/687,181

(22) Filed: Aug. 25, 2017

Related U.S. Application Data

(60) Provisional application No. 62/528,747, filed on Jul. 5, 2017.

(51) Int. Cl.
| | | |
|---|---|---|
| *C07C 231/00* | (2006.01) | |
| *C07C 269/06* | (2006.01) | |
| *C07D 231/40* | (2006.01) | |
| *B01J 31/02* | (2006.01) | |

(52) U.S. Cl.
CPC ......... *C07C 231/00* (2013.01); *B01J 31/0271* (2013.01); *C07C 269/06* (2013.01); *C07D 231/40* (2013.01); *B01J 2231/40* (2013.01); *B01J 2531/002* (2013.01); *C07C 2601/14* (2017.05)

(58) Field of Classification Search
None
See application file for complete search history.

(56) References Cited

U.S. PATENT DOCUMENTS

| | | | |
|---|---|---|---|
| 7,838,680 B2 | 11/2010 | Bacchi | |
| 2007/0161813 A1* | 7/2007 | Meudt | C07C 253/20 558/382 |
| 2016/0340328 A1* | 11/2016 | Dowdell | C07D 407/04 |

FOREIGN PATENT DOCUMENTS

WO     2007/012387 A1    2/2007

OTHER PUBLICATIONS

Sambaiah, et al., Tet. Lett., 57:403 (2016, available online Dec. 8, 2015). (Year: 2016).*
Kooti, M., et al., "Phosphotungstic Acid Supported on Silica-Coated $CoGFe_2O_4$ Nanoparticles: An Efficient and Magnetically-Recoverable Catalyst for N-Formylation of Amines under Solvent-Free Conditions", Journal of Molecular Catalysts A: Chemical, vol. 406, 3 Pages total, (Sep. 2015) (Abstract only).
Bannwart, L., et al., "Metal-Free Amidation of Acids with Formamides and T3P", Synthesis, URL: https://www.thieme-connect.com/products/ejournals/abstract/10.1055/s-0035-1561427, vol. 48, No. 13, 2 Pages total, (Apr. 12. 2016) (Abstract only).
Joseph, S., et al., "A Convenient Procedure for N-Formylation of Amines", Tetrahedron Letters, vol. 54, Issue 8, 3 Pages total, (Feb. 20, 2013) (Abstract only).
Hosseini-Sarvari, M., et al., "ZnO as a New Catalyst for N-Formylation of Amines under Solvent-Free Conditions", The Journal of Organic Chemistry, vol. 71, pp. 6652-6654, (Jul. 28, 2006).
Majumdar, S., et al., "Formylation of Amines Catalysed by Protic Ionic Liquids under Solvent-Free Condition", Tetrahedron Letters, vol. 54, pp. 262-266, (2013).
Dhake, K.P., et al., "An Efficient, Catalyst- and Solvent-Free N-Formylation of Aromatic and Aliphatic Amines", Green Chemistry Letters and Reviews, vol. 4, No. 2, pp. 151-157, (Mar. 9, 2011).
Bahari, S., et al., "An Efficient Method for N-Formylation of Amines Using Natural HEU Zeolite at Room Temperature Under Solvent-Free Conditions", Bulletin—Korean Chemical Society, vol. 33, No. 7, pp. 2251-2254, (Jul. 2012)
Augustine, J.K., et al., "An Efficient Catalytic Method for the Beckmann Rearrangement of Ketoximes to Amides and Aldoximes to Nitriles Mediated by Propylphosphonic Anhydride (T3P)", Tetrahedron Letters, vol. 52, pp. 1074-1077, (Dec. 29, 2010).
Shastri, L.A., et al., "Mild, Simple, and Efficient Method for N-Formylation of Secondary Amines via Reimer-Tiemann Reaction", Synthetic Communications, vol. 41, pp. 476-484, (Feb. 2, 2011).
Augustine, J.K., "An Efficient Catalytic Method for the Friedländer Annulation Mediated by Peptide Coupling Agent Propylphosphonic Anhydride (T3P)", Tetrahedron Letters, vol. 52, pp. 6814-6818, (Oct. 15, 2011).
Blicke, F.F., et al., "Formylation of Amines with Chloral and Reduction of the N-Formyl Derivatives with Lithium Aluminum Hydride", Journal of the American Chemical Society, vol. 74, No. 15, pp. 3933-3934, (Aug. 1952).
Waki, M., et al., "Efficient Preparation of Nα-Formylamino Acid tert-Butyl Esters", The Journal of Organic Chemistry, vol. 42, No. 11, pp. 2019-2020, (1977).
Ganapati Reddy, P., et al., "A Convenient Method for the N-formylation of Secondary Amines and Anilines using Ammonium Formate", Tetrahedron Letters, vol. 41, pp. 9149-9151, (2000).
De Luca, L., et al., "A New, Simple Procedure for the Synthesis of Formyl Amides", Synlett, URL: https://www.thieme-connect.com/products/ejournals/abstract/10.1055/s-2004-834788, vol. 14, 5 Pages total, (Sep. 28, 2004) (Abstract only).
Cochet, T., et al., "N-Formylsaccharin: A New Formylating Agent", Synlett, URL: https://www.thieme-connect.com/products/ejournals/abstract/10.1055/s-0030-1260951, vol. 13, 5 Pages total, (Jul. 14, 2011) (Abstract only).
Kaboudin, B., et al., "Organic Reactions in Water: A Practical and Convenient Method for the N-Formylation of Amines in Water", Synlett, URL: https://www.thieme-connect.com/products/ejournals/abstract/10.1055/s-0030-1259029 vol. 19, 5 Pages total, (Nov. 10, 2010) (Abstract only).
Kim, J., et al., "Facile and Highly Efficient N-Formylation of Amines Using a Catalytic Amount of Iodine under Solvent-Free Conditions", Synlett, URL: https://www.thieme-connect.com/products/ejournals/abstract/10.1055/s-0030-1258518, vol. 14, 6 Pages total, (Jul. 22, 2010) (Abstract only).
Chandra Shekhar. A., et al., "Facile N-formylation of Amines using Lewis Acids as Novel Catalysts", Tetrahedron Letters, vol. 50, pp. 7099-7101, (Oct. 8, 2009).

* cited by examiner

*Primary Examiner* — Michael Barker
(74) *Attorney, Agent, or Firm* — Oblon, McClelland, Maier & Neustadt, L.L.P.

(57) ABSTRACT

A method for N-formylating an amine that includes reacting the amine and a formamide compound in the presence of a phosphonic anhydride to form an N-formylated amine. The phosphonic anhydride is present in an amount of 5-100 mol % relative to a total number of moles of the amine, and the reacting is performed for 1-24 hours at a temperature of 45-100° C.

17 Claims, 2 Drawing Sheets

METHOD OF N-FORMYLATING AMINES WITH A PHOSPHONIC ANHYDRIDE

RELATED APPLICATIONS

This application claims the priority of the filing date of the U.S. Provisional Patent Application No. 62/528,747 filed Jul. 5, 2017, the disclosure of which is hereby incorporated herein by reference in its entirety.

BACKGROUND OF THE INVENTION

Technical Field

The present disclosure relates to a method of N-formylating an amine with a formamide compound using a phosphonic anhydride catalyst.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

The formyl group is an important amino-protecting group in peptide synthesis [Hartinez, J.; Laur, J. Synthesis 1982, 979] and formamides are regarded as useful intermediates in organic synthesis and medicinal chemistry [Kobayashi, K.; Nagato, S.; Kawakita, M.; Morikawa, O.; Konishi, H. Chem. Lett. 1995, 575; Chen, B. C.; Bednarz, M. S.; Zhao, R.; Sundeen, J. E.; Chen, P.; Shen, Z.; Skoumbourdis, A. P.; Barrish, J. C. Tetrahedron Lett. 2000, 41, 5453]. In addition, formamides are well-known reagents having a wide range of applications in organic synthesis such as allylation [Kobayashi, S.; Nishio, K. J. Org. Chem. 1994, 59, 6620], hydrosilylation [Kobayashi, S.; Yasuda, M.; Hachiya, I. Chem. Lett. 1996, 407], Vilsmeier reactions [Downie, I. M.; Earle, M. J.; Heaney, H.; Shuhaibar, K. F. Tetrahedron 1993, 49, 4015], synthesis of formamidines [Han, Y.; Cai, L. Tetrahedron Lett. 1997, 38, 5423], fluroquinolones [Jackson, A.; Meth-Cohn, O. J. Chem. Soc., Chem. Commun. 1995, 1319-1320], substituted aryl imidazoles [Chen, B.-C.; Bednarz, M. S.; Zhao, R.; Sundeen, J. E.; Chen, P.; Shen, Z.; Skoumbourdis, A. P.; Barrish, J. C. Tetrahedron Lett. 2000, 41, 5453-5456], 1,2-dihydroquinoinolines [Kobayashi, K.; Nagato, S.; Kawakita, M.; Morikawa, O.; Konishi, H. Chem. Lett. 1995, 575-576], and nitrogen bridged heterocycles [Kakehi, A.; Ito, S.; Hayashi, S.; Fujii, T. Bull. Chem. Soc. Jpn. 1995, 68, 3573-3580], among others.

In the literature, various approaches are available for N-formylation using different reagents such as chloral [Blicke, F. F.; Lu, C.-J. J. Am. Chem. Soc. 1952, 74, 3933], formic acid-DCC [Waki, J.; Meinhofer, J. J. Org. Chem. 1977, 42, 2019], formic acid-EDCI [Chen, F. M. F.; Benoiton, N. L. Synthesis 1979, 709], formic acid in toluene [Jung, H. S.; Ahn, J. H.; Park, S. K.; Choi, J. K. Bull. Korean Chem. Soc. 2002, 23, 149], ammonium formate [Reddy, P. G.; Kumar, G. D. K.; Bhaskaran, S. Tetrahedron 2000, 41, 9149], CDMT [Luca, L. D.; Giacomelli, G.; Porcheddu, A.; Salaris, M. Synlett 2004, 2570], KF-alumina, and other solid-supported reagents [Mihara, M.; Ishino, Y.; Minakara, S.; Komatsu, M. Synthesis 2003, 2317; Hosseini-Sarvari, M.; Sharghi, H. J. Org. Chem. 2008, 71, 6652; Das, B.; Krishnaiah, M.; Balasubramanyam, P.; Veeranjaneyulu, B.; Nandan kumar, D. Tetrahedron Lett. 2008, 49, 2225; Firouzabadi, H.; Iranpoor, N.; Farahi, S. J. Mol. Catal. A: Chem. 2008, 289, 61; Niknam, K.; Saberi, D. Tetrahedron Lett. 2009, 50, 5210]. Most recently N-formylation using Methyl benzoate [Yang, D; Jeon, H. B. Bull. Korean Chem. Soc. 2010, Vol. 31, No. 5], $ZnCl_2$, $FeCl_3$, $AlCl_3$, and $NiCl_2$ has been reported [Chandra Shekhar, A.; Ravi Kumar, A.; Sathaiah, G.; Luke Paul, V.; Sridhar, M.; Shanthan Rao, P. Tetrahedron Lett. 2009, 50, 7099]. However such methods have drawbacks including the use of toxic reagents, the use of expensive reagents or reagents that are difficult to access, thermally unstable reagents, the formation of side products, and the lack of functional group tolerance. Therefore, it is desirable to develop improved methods that are efficient, general, that operate under mild reaction conditions, that use non-toxic reagents, that can be performed on large-scale, that have simple work-up procedures, and that have high functional group tolerance.

Propylphosphonic anhydride (T3P) is a mild water scavenger with low toxicity and low allergenic potential [For a brief review of the reagent, see: Llanes Garcia, A. L. Synlett 2007, 1328; Schwarz, M. Synlett 2000, 1369]. Although T3P has been largely used as a mild coupling reagent in peptide synthesis, new applications have recently been developed for this reagent [For other applications of T3P, see: Burkhart, F.; Hoffmann, M.; Kessler, H. Angew. Chem., Int. Ed. 1997, 36, 1191; Wedel, M.; Walter, A.; Montforts, F.-P. Eur. J. Org. Chem. 2001, 1681; Hermann, S. Ger. Offen. DE 10063493, 2002; Chem. Abstr. 2002, 137, 47003.; Meudt, A.; Scherer, S.; Nerdinger, S. PCT Int. Appl. WO 2005070879, 2005; Chem. Abstr. 2005, 143, 172649.; Meudt, A.; Scherer, S.; Böhm, C. PCT Int. Appl. WO 2005102978, 2005; Chem. Abstr. 2005, 143, 440908.; Zumpe, F. L.; Melanie, F.; Schmitz, K.; Lender, A. Tetrahedron Lett. 2007, 48, 1421; Augustine, J. K.; Atta, R. N.; Ramappa, B. K.; Boodappa, C. Synlett 2009, 3378; Augustine, J. K.; Vairaperumal, V.; Narasimhan, S.; Alagarsamy, P.; Radhakrishnan, A. Tetrahedron 2009, 65, 9989; James, M.; Crawforth, J. M.; Paoletti, M. Tetrahedron Lett. 2009, 50, 4916; Vasantha, B.; Hemantha, H. P.; Sureshbabu, V. V. Synthesis 2010, 2990].

Therefore, one objective of the present disclosure is to provide a method of N-formylating an amine using a phosphonic anhydride catalyst and a formamide formylating agent to overcome many of the drawbacks listed above.

BRIEF SUMMARY

According to a first aspect, the present disclosure relates to a method for N-formylating an amine involving reacting the amine and a formamide compound in the presence of a phosphonic anhydride to form an N-formylated amine.

In one embodiment, the formamide compound is of formula (I):

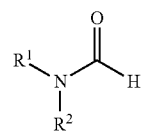

wherein $R^1$ and $R^2$ are independently H, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, or an optionally substituted hydrocarbyl, with $R^1$ and $R^2$ also being able to form, together with the nitrogen atom to which they are bound, a saturated or unsaturated 3- to 6-membered heterocyclic ring.

In one embodiment, $R^1$ and $R^2$ are independently an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, or an optionally substituted hydrocarbyl.

In one embodiment, $R^1$ and $R^2$ are independently an optionally substituted alkyl.

In a preferred embodiment, $R^1$ and $R^2$ are each methyl.

In one embodiment, the formamide compound is present in an amount of at least 5 mole equivalents relative to a total number of moles of the amine.

In one embodiment, the phosphonic anhydride is of formula (II):

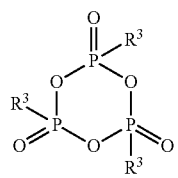

(II)

wherein each $R^3$ is independently an optionally substituted alkyl, an optionally substituted cycloalkyl, an optionally substituted cycloalkylalkyl, an optionally substituted arylalkyl, an optionally substituted aryl, or an optionally substituted hydrocarbyl.

In one embodiment, each $R^3$ is the same.

In one embodiment, $R^3$ is an optionally substituted alkyl.

In one embodiment, $R^3$ is propyl.

In one embodiment, the phosphonic anhydride is present in an amount of 5-100 mol % relative to a total number of moles of the amine.

In one embodiment, the phosphonic anhydride is present in an amount of 10-30 mol % relative to a number of moles of the amine.

In one embodiment, the amine is of formula (III):

$$R^4\text{—}NH_2 \qquad (III)$$

wherein $R^4$ is H, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, or an optionally substituted hydrocarbyl.

In one embodiment, the amine is an optionally substituted arylamine of formula (IV):

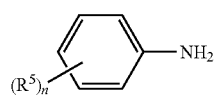

(IV)

wherein
each $R^5$ is an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted hydrocarbyl, an optionally substituted alkoxy, an optionally substituted cycloalkyloxy, an optionally substituted aryloxy, an optionally substituted arylalkyloxy, an optionally substituted aroyl, an optionally substituted alkanoyl, an optionally substituted alkanoyloxy, a carboxy, an optionally substituted alkoxycarbonyl, a hydroxyl, a halo, an amino group of the formula —$NH_2$, —$NHR^6$, or —$N(R^6)_2$, nitro, cyano, an optionally substituted carbamyl, a thiol, an optionally substituted alkylthio, an optionally substituted arylthio, an optionally substituted arylalkylthio, an optionally substituted alkylsulfonyl, an optionally substituted arylsulfonyl, an optionally substituted arylalkylsulfonyl, and an optionally substituted sulfonamido (e.g. —$SO_2NH_2$);

each $R^6$ is independently an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted hydrocarbyl, an optionally substituted aroyl, an optionally substituted alkanoyl, an optionally substituted alkoxycarbonyl, an optionally substituted carbamyl, an optionally substituted alkylsulfonyl, an optionally substituted arylsulfonyl, an optionally substituted arylalkylsulfonyl, and an optionally substituted sulfonamido (e.g. —$SO_2NH_2$); and n is an integer of 0-5.

In one embodiment, the method in one or more of its embodiments, further includes at least one organic solvent selected from the group consisting of tetrahydrofuran, acetonitrile, dioxane, toluene, ethylene dichloride, ethyl acetate, and nitromethane.

In one embodiment, the reacting is performed for 1-24 hours at a temperature of 45-100° C.

In one embodiment, the formamide compound is present in an amount of at least 10 mole equivalents, the phosphonic anhydride is present in an amount of 10-30 mol %, and the N-formylated amine is formed in an isolated yield of at least 80%, each based on a total number of moles of the amine.

In one embodiment, the reacting is performed by adding a phosphonic anhydride solution comprising the phosphonic anhydride and an organic solvent to a mixture of the amine and the formamide compound.

In one embodiment, the phosphonic anhydride is the only compound present that catalyzes the reaction between the amine and the formamide compound (i.e. the only formylating catalyst present).

In one embodiment, the formamide compound is the only formylating agent present.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
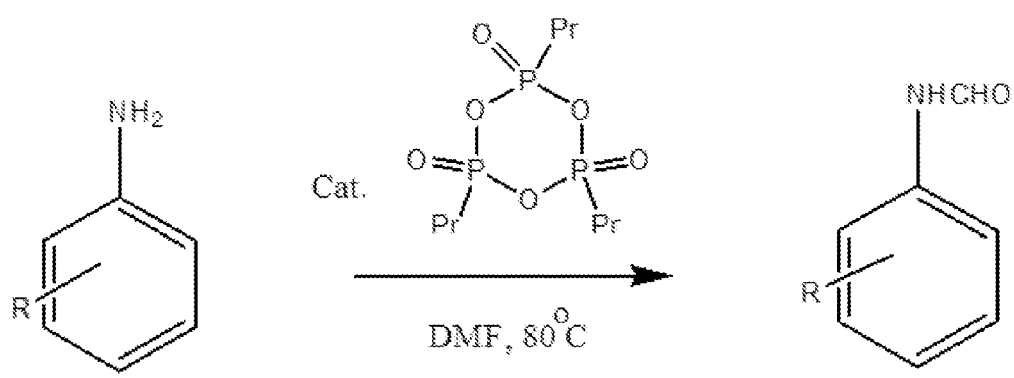
FIG. 1 is a general reaction scheme for the N-formylation of arylamines with propylphosphonic anhydride (T3P®).

Embodiments of the present disclosure will now be described more fully hereinafter with reference to the accompanying drawings, in which some, but not all of the embodiments of the disclosure are shown.

The present disclosure will be better understood with reference to the following definitions.

As used herein, the words "a" and "an" and the like carry the meaning of "one or more". Additionally, within the description of this disclosure, where a numerical limit or range is stated, the endpoints are included unless stated otherwise. Also, all values and subranges within a numerical limit or range are specifically included as if explicitly written out.

As used herein, the terms "optional" or "optionally" means that the subsequently described event(s) can or cannot occur or the subsequently described component(s) may or may not be present (e.g. 0 wt %).

When referencing reaction components or materials present in the method for N-formylating an amine, the phrase "substantially free", unless otherwise specified, describes an amount of a particular component(s) that may be present in an amount of less than about 1 wt %, less than about 0.5 wt %, less than about 0.3 wt %, less than about 0.2 wt %, less than about 0.1 wt %, less than about 0.01 wt %, preferably about 0 wt %, relative to a total weight of the reaction components (e.g. the amine, the formamide compound, the phosphonic anhydride, the optional organic solvent, etc.).

The term "comprising" is considered an open-ended term synonymous with terms such as including, containing or having and is used herein to describe aspects of the invention which may include additional reaction steps, components, functionality and/or structure. Terms such as "consisting essentially of" are used to identify aspects of the invention which exclude particular components or process steps that are not explicitly recited in the claim but would otherwise have a material effect on the basic and novel outcomes/properties of the methods or compositions used or produced in the methods. Basic and novel outcomes/properties of the present disclosure include the reaction conversion, reaction yield, reaction parameters (e.g. pressure, temperature, reaction time, etc.) needed to reach a particular yield or conversion, and so forth. The term "consisting of" describes aspects of the invention in which only those features explicitly recited in the claims are included and thus other components or process steps not explicitly or inherently included in the claim are excluded.

As used herein, the term "compound" is intended to refer to a chemical entity, whether in the solid, liquid or gaseous phase, and whether in a crude mixture or purified and isolated. The term "derivative" or "analog" refers to a chemically modified version of a chemical compound that is structurally similar to a parent compound.

The term "catalyst" and "promoter" are used interchangeably herein with respect to reactions that involve the N-formylation of an amine to form an N-formylated amine. These terms are used to describe species that increase the rate of a chemical reaction (e.g. N-formylation reaction) or allow the reaction to proceed, but do not appear in the final product. Further, there is no requirement that the catalyst or promoter is regenerated during the reaction, or is used in sub-stoichiometric amounts. Rather, the catalyst or promoter is defined by the characteristic that it increases the rate of reaction or allows the reaction to proceed when it otherwise wouldn't, regardless of whether the catalyst or promoter is present in sub-stoichiometric amounts (e.g. 25 mole %), stoichiometric amounts (e.g. 100 mol %), or super stoichiometric amounts (e.g. 1,000 mol %), and regardless of whether the catalyst/promoter has the same structure at the end of a reaction cycle.

The term "alkyl", as used herein, unless otherwise specified, refers to a straight, branched, or cyclic hydrocarbon fragment. Non-limiting examples of such hydrocarbon fragments include those having 1 to 32 carbon atoms and specifically includes methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, and unsaturated alkenyl and alkynyl variants such as vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, and the like. As used herein, the term "cycloalkyl" or "cyclic hydrocarbon" refers to a cyclized alkyl group. Exemplary cyclic hydrocarbon (i.e. cycloalkyl) groups include, but are not limited to, cyclopropyl, cyclobutyl, cyclopentyl, cyclohexyl, norbornyl, and adamantyl. Branched cycloalkyl groups, such as 1-methylcyclopropyl and 2-methycyclopropyl groups and alkyl groups substituted with cycloalkyl groups (cycloalkylalkyl groups such as cyclohexylmethyl) are included in the definition of alkyl in the present disclosure. Furthermore, the term "cycloalkenyl" is included in the definition of alkyl, which refers to cyclized alkenyl groups including C4, C5, and C6 cycloalkenyl groups. Example cycloalkenyl groups include, but are not limited to, cyclobutenyl, cyclopentenyl, and cyclohexenyl.

The term "hydrocarbyl" as used herein refers to a univalent hydrocarbon group containing up to about 24 carbon atoms (i.e., a group containing only carbon and hydrogen atoms) and that is devoid of olefinic (i.e. alkenyl) and acetylenic (i.e. alkynyl) unsaturation, and includes alkyl, cycloalkyl, cycloalkylalkyl, aryl, alkylaryl, arylalkyl. These groups may be optionally substituted and still meet the definition of hydrocarbyl so long as the optional substituent is not alkenyl or alkynyl.

The term "haloalkyl" refers to straight or branched chain alkyl groups having 1 to 32 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-tri-fluoroethyl, 2,3,3-trifluoropropyl, 1,1,2,2-tetrafluoroethyl, 2,2,3,3-tetrafluoropropyl.

The term "heterocyclyl" as used in this disclosure refers to a 3-10, preferably 4-8, more preferably 4-7 membered monocyclic ring, a fused 8-12 membered bicyclic ring which may be saturated or partially unsaturated, or a 7-, 8-, 9-, 10-, 11-, 12-, 13-, or 14-membered polycyclic heterocyclic ring that is saturated, partially unsaturated, or fully unsaturated, which monocyclic, bicyclic, or polycyclic ring contains 1 to 4 heteroatoms selected from oxygen, nitrogen, silicon or sulfur. Examples of such monocyclic rings include oxaziridinyl, homopiperazinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl and azepanyl. Examples of such bicyclic rings include indolinyl, isoindolinyl, benzopyranyl, quinuclidinyl, 2,3,4,5-tetrahydro-1,3,benzazepine, 4-(benzo-1,3,dioxol-5-methyl)piperazine, and tetrahydroisoquinolinyl. Examples of heterocycles include, but are not limited to, acridinyl, azetidinyl, azocinyl, benzimidazolyl, ben-zofuranyl, benzothiofuranyl, benzothiophenyl, benzox-azolyl, benzoxazolinyl, benzthiazolyl, benztriazolyl, benztetrazolyl, benzisoxazolyl, benzisothiazolyl, benzimida-zolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indoliz-inyl, indolyl, 3H-indolyl, isatinoyl, isobenzofuranyl, isochro-manyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1.2.4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenan-throlinyl, phenazinyl, phenothiazinyl, phenoxathiinyl, phe-noxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopy-ridinyl, pyrazolyl, pyridazinyl, pyridooxazolyl, pyridoimida-zolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1.2.4-thiadiazolyl, 1,2,5-thiadiazolyl, 1,3,4-thiadiazolyl, thianthrenyl, thiazolyl, thienyl, thiazolopyridinyl, thienothiaz-olyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles. Further, "substituted heterocyclyl" may refer to a heterocyclic ring which has one or more oxygen, nitrogen, or sulfur atoms bonded to a carbon or heteroatom within cyclic ring, for example, 1,1-dioxido-1,3-thiazolidinyl.

The term "aryl", as used herein, and unless otherwise specified, refers to an aromatic group containing only carbon in the aromatic ring(s), such as phenyl, biphenyl, naphthyl, anthracenyl, and the like. The term "heteroaryl" refers to an aryl group where at least one carbon atom is replaced with a heteroatom (e.g. nitrogen, oxygen, sulfur) and includes, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)p, wherein p is 0, 1 or 2). Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "arylalkyl" as used in this disclosure refers to a straight or branched chain alkyl moiety having 1 to 32 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl.

An "alkoxy" group is a straight or branched chain alkyl group having 1 to 32 carbon atoms bound to oxygen (—Oalkyl), and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy and decyloxy. "Cycloalkyloxy" is a cyclic variant of alkoxy and includes cyclopentyloxy, cyclohexyloxy, and cycloheptyloxy. "Aryloxy" refers to an aryl group bound to oxygen (—Oaryl), e.g. phenoxy, p-tolyloxy, etc. "Arylalkyloxy" refers to arylalkyl groups where the alkyl portion is bound to oxygen (—Oalkylaryl) and includes benzyloxy, 2-phenethoxy, and the like.

"Aroyl" refers to aryl carbonyl (arylC(O)—) substituents such as benzoyl and naphthoyl while "alkanoyl" refers to alkyl variants (alkylC(O)—), where the alkyl group is bound to a carbon that is attached to an oxygen atom through a double bond. Examples of alkanoyl substitution includes, acetyl, propionyl, butyryl, isobutyryl, pivaloyl, valeryl, hexanoyl, octanoyl, lauroyl, and stearoyl. As used herein, "alkanoyloxy" groups are alkanoyl groups that are bound to oxygen (—O—C(O)-alkyl), for example, acetyloxy, propionyloxy, butyryloxy, isobutyryloxy, pivaloyloxy, valeryloxy, hexanoyloxy, octanoyloxy, lauroyloxy, and stearoyloxy. "Alkoxycarbonyl" substituents are alkoxy groups bound to C=O (e.g. —C(O)—Oalkyl), for example methyl ester, ethyl ester, and pivaloyl ester substitution where the carbonyl functionality is bound to the rest of the compound. The term "heteroarylcarbonyl" as used in this disclosure refers to a heteroaryl moiety with 5 to 10 membered mono- or fused-heteroaromatic ring having at least one heteroatom selected from nitrogen, oxygen and sulfur as mentioned above, and includes, for example, furoyl, nicotinoyl, isonicotinoyl, pyrazolylcarbonyl, imidazolylcarbonyl, pyrimidinylcarbonyl, benzimidazolyl-carbonyl.

The term "alkylthio", "arylthio" or "arylalkylthio" as used in this disclosure refers to a divalent sulfur with alkyl, aryl, or arylalkyl groups, respectively, occupying one of the valencies. For example, alkylthio may be methylthio, ethylthio, propylthio, butylthio, pentylthio, hexylthio, octylthio and the like.

As used herein, the term "substituted" refers to at least one hydrogen atom that is replaced with a non-hydrogen group, provided that normal valencies are maintained and that the substitution results in a stable compound. When a compound or a R group (denoted as $R_1$, $R_2$, and so forth) is noted as "optionally substituted", the substituents are selected from the exemplary group including, but not limited to, alkyl, cycloalkyl, cycloalkylalkyl, arylalkyl, heteroaryl, aryl, heterocyclyl, hydrocarbyl, alkoxy, cycloalkyloxy, aryloxy, arylalkyloxy, aroyl, alkanoyl, alkanoyloxy, carboxy, alkoxycarbonyl, hydroxyl, halo (e.g. chlorine, bromine, fluorine or iodine), amino (e.g. alkylamino, arylamino, arylalkylamino, alkanoylamino, either mono- or disubstituted), nitro, cyano, carbamyl, a thiol, alkylthio, arylthio, arylalkylthio, alkylsulfonyl (i.e. —SO₂alkyl), arylsulfonyl (i.e. —SO₂aryl), arylalkylsulfonyl (i.e. —SO₂arylalkyl), sulfonamido (e.g. —SO₂NH₂, —SO₂NHalkyl, —SO₂NHaryl, —SO₂NHarylalkyl or cases with two substituents on one nitrogen atom), haloalkyl, oxo, carbamyl (e.g. —CONH₂, —CONHalkyl, —CONHaryl, —CONHarylalkyl or cases where there are two substituents on one nitrogen), guanidino, heteroarylcarbonyl, and mixtures thereof and the like. The substituents may themselves be optionally substituted, and may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety).

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include ¹³C and ¹⁴C. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

According to a first aspect, the present disclosure relates to a method for N-formylating an amine involving reacting a mixture comprising, consisting essentially of, or consisting of the amine, a formamide compound, and a phosphonic anhydride to form an N-formylated amine.

Formamide Compound

Formamide functionality is an amide theoretically derived from formic acid, i.e. has a general formula R₂NC(O)H. The formamide compound is employed in the disclosed method as a formylating agent or a formyl donor. The formamide compound functions in the method by transferring a formyl group (—C(O)H) to the amine being formylated to form an N-formylated amine and an amine byproduct (R₂NH) as a result of de-formylation of the formamide compound. Not all formylating agents or formyl donors formally transfer a formyl group in such a manner, for example in various catalyzed methods, the formyl group is formed in situ or during the formylation reaction pathway. For example, carbon monoxide and hydrogen mixtures can be used as a formylating agent/formyl donor, even though no formyl —C(O)H functionality is present in CO or H₂. Therefore, "formylating agent" or "formyl donor" as used herein refers to the source of the formyl functionality found in the resulting N-formylated product, and need not contain a formyl functional group itself. Examples of formylating agents deployed in chemical or biochemical formylation reactions include formic acid, formic acid/sodium formate mixtures, carbon monoxide, carbon dioxide and a hydrogen source (e.g. H₂), carbon monoxide and a hydrogen source (e.g. H₂), formyl halides (e.g. formyl fluoride, formyl chloride, formyl bromide, formyl iodide), formyl cyanide, chloral (trichloroacetaldehyde), formic anhydride, acetic formic anhydride (AFA), ammonium formate, cyanoalkyl formates (e.g. cyanomethylformate), alkyl formates (e.g. methyl formate), Reimer-Tiemann reagents prepared from chloroform and alkoxide salts (e.g. sodium ethoxide), trialkyl orthoformates (e.g. triethyl orthoformate), paraformaldehyde, methanol (e.g. under oxidative conditions), succinimidyl esters (e.g. 2,5-dioxopyrrolidin-1-yl formate), and metal carbonyls (e.g. W(CO)₆).

In one embodiment, the formamide compound is of formula (I):

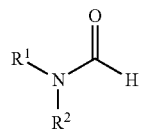

wherein R¹ and R² are independently H, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, or an optionally substituted hydrocarbyl, with R¹ and R² also being able to form, together with the nitrogen atom to which they are bound, a saturated or unsaturated 3- to 6-membered heterocyclic ring. For example, R¹ and R² together with the nitrogen atom may form an optionally substituted aziridine, an optionally substituted azetidine, an optionally substituted pyrrolidine, an optionally substituted piperidine, an optionally substituted 91H-carbazole, an optionally substituted 9,10-dihydroacridine, an optionally substituted 5,10-dihydrophenazine, an optionally substituted indole, an optionally substituted pyrrole, an optionally substituted 2- or 3-pyrroline, an optionally substituted 2-imidazoline, an optionally substituted imidazolidine, an optionally substituted imidazole, an optionally substituted benzimidazole, an optionally substituted piperazine, an optionally substituted morpholine, or an optionally substituted phenoxazine, to form exemplary formamide compounds aziridine-1-carbaldehyde, azetidine-1-carbaldehyde, pyrrolidine-1-carbaldehyde, piperidine-1-carbaldehyde, 9H-carbazol-9-carbaldehyde, acridine-10(9H)-carbaldehyde, phenazine-5(10H)-carbaldehyde, indole-1-carbaldehyde, pyrrole-1-carbaldehyde, 2- or 3-pyrroline-1-carbaldehyde, 2-imidazoline-1-carbaldehyde, imidazolidine-1-carbaldehyde, imidazole-1-carbaldehyde, benzimidazole-I-carbaldehyde, piperazine-1-carbaldehyde, morpholine-4-carbaldehyde, phenoxazine-10-carbaldehyde, and the like.

In one embodiment, R¹ and R² do not together with the nitrogen atom to which they are bound form a ring, and instead are not connected. The formamide compound of formula I preferably has R¹ and R² groups which are independently an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, or an optionally substituted hydrocarbyl.

Preferably, neither R¹ or R² is a hydrogen atom. In one embodiment, R¹ and R² are independently an optionally substituted alkyl group, preferably having 1-20 carbon atoms, or 1-16 carbon atoms, or 1-10 carbon atoms, or 2-8 carbon atoms, or 3-6 carbon atoms, or 4-5 carbon atoms, or 1-4 carbon atoms, or 1-3 carbon atoms, or 1-2 carbon atoms. Preferably, each R¹ and R² are independently an optionally substituted alkyl group having 1-4 carbon atoms, for example N,N-dimethylformamide, N,N-diethylformamide, N,N-dibutylformamide, and N,N-diisopropylformamide. In a preferred embodiment, R¹ and R² are each an optionally substituted alkyl group having 1 carbon atom, preferably methyl, and the formamide compound is N,N-dimethylformamide (DMF).

In one embodiment, mixtures of formamide compounds of formula I (e.g. N,N-dimethyl formamide and N,N-diethylformamide) may be employed in the N-formylation reaction. When present as a mixture of first and second formamide compounds, the formamide compounds may be present in a molar ratio of 1:10 to 10:1, 2:8 to 8:2, 3:7 to 7:3, 4:6 to 6:4, or about 1:1.

The formamide compound may be miscible in organic solvents (described hereinafter), in aqueous solvents (e.g. water), or both organic solvents and aqueous solvents. Preferably the formamide compound has a melting point below room temperature (about 20° C. to 25° C.) such as −100° C. to −20° C., −80° C. to −40° C., −70° C. to −50° C., or about −60.5° C. at standard atmosphere (1 atm), and thus is in the liquid phase at standard atmosphere and temperature. Preferably, the formamide compound is selected such that the amine byproduct after formyl transfer (i.e. $R_1R_2NH$) is soluble in water and can thus be easily removed from the N-formylated amine product.

The formamide compound may be present during the reacting (i.e. as a formylating agent or formyl donor) in an amount of at least 5 mole equivalents, at least 6 mole equivalents, at least 7 mole equivalents, at least 8 mole equivalents, at least 9 mole equivalents, at least 10 mole equivalents, at least 12 mole equivalents, and up to 50 mole equivalents, up to 40 mole equivalents, up to 30 mole equivalents, or up to 20 mole equivalents, relative to a total number of moles of the amine. Preferably, the formamide compound is used in solvent quantities (i.e. greater than 12 mole equivalents). When the formamide compound is employed in solvent quantities, the molar concentration (Molarity, mol/L) of the amine in the formamide compound is 0.05-5 M, 0.1-4 M, 0.5-3 M, 0.8-2 M, 0.9-1.5 M, 0.95-1.2 M, or about 1M.

In one embodiment, the formamide compound may be used in combination with other formylating agents or formyl donors. In one embodiment, the formamide compound of formula I (or mixtures of compounds thereof) is the only formylating agent present, and no other formylating agents or formyl donors are included as starting materials in the method of N-formylating the amine. In particular, the method is substantially free of one or more of formic acid, sodium formate, carbon monoxide and/or carbon dioxide (with or without a hydrogen source e.g. $H_2$), formyl halides (e.g. formyl fluoride, formyl chloride, formyl bromide, formyl iodide), formyl cyanide, chloral (trichloroacetaldehyde), formic anhydride, acetic formic anhydride (AFA), ammonium formate, cyanoalkyl formats (e.g. cyanomethylformate), alkyl formats (e.g. methyl formate), Reimer-Tiemann reagents, trialkyl orthoformates (e.g. triethyl orthoformate), paraformaldehyde, methanol (e.g. under oxidative conditions), succinimidyl esters (e.g. 2,5-dioxopyrrolidin-1-yl formate), and metal carbonyls (e.g. $W(CO)_6$).

Phosphonic Anhydride

Phosphonic anhydrides are oxophilic desiccants and/or dehydrating agents derived from phosphonic acids that can be in the form of polymers or oligomers of open chain phosphonic acid condensation products or cyclic phosphonic anhydride analogs thereof, preferably cyclic trimeric analogs. Cyclic phosphonic anhydrides are commonly used as promoters in amide coupling reactions between a carboxylic acid and an amine, whereby a carboxylic acid or carboxylate anion nucleophile attacks the cyclic phosphonic anhydride to form an activated ester, which in turn acts as an electrophile in a reaction with the amine resulting in amide bond formation.

In the present method, the phosphonic anhydride preferably has a boiling point of 50-90° C., 55-85° C., 60-80° C., or about 65° C. at 1 atm pressure, and is also preferably water soluble which may aid separation of the phosphonic anhydride or byproducts thereof from the N-formylated amine after reaction completion. In some embodiments, the phosphonic anhydride can be added to the reaction as a mixture with an organic solvent or the formamide compound. For example, when the formamide compound is dimethyl formamide (DMF), a portion or all of the formamide compound (DMF) can be used to dissolve and/or transfer the phosphonic anhydride as a solution for reacting with the amine component.

In one embodiment, the phosphonic anhydride of the present disclosure is a cyclic phosphonic anhydride of formula (II):

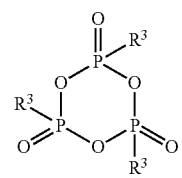

(II)

wherein each $R^3$ is independently an optionally substituted alkyl, an optionally substituted cycloalkyl, an optionally substituted cycloalkylalkyl, an optionally substituted arylalkyl, an optionally substituted aryl, or an optionally substituted hydrocarbyl. Each $R^3$ may be the same, or different. Preferably each $R^3$ is the same.

In one embodiment, $R^3$ is an optionally substituted alkyl group, preferably having 1-20 carbon atoms, or 1-16 carbon atoms, or 1-10 carbon atoms, or 2-8 carbon atoms, or 3-6 carbon atoms, or most preferably 3-4 carbon atoms. For example, the phosphonic anhydride of formula II may be ethylphosphonic anhydride, propylphosphonic anhydride, isopropylphosphonic anhydride, butylphosphonic anhydride, hexylphosphonic anhydride, or cyclohexylphosphonic anhydride. In a preferred embodiment, each $R^3$ is propyl, and the phosphonic anhydride is propylphosphonic anhydride (T3P®, Archimica GmbH).

In one embodiment, mixtures of phosphonic anhydride compounds of formula II (e.g. propylphosphonic anhydride and cyclohexylphosphonic anhydride) may be employed in the N-formylation reaction. When present as a mixture of a first and second phosphonic anhydride, the phosphonic anhydrides may be present in a molar ratio of 1:10 to 10:1, 2:8 to 8:2, 3:7 to 7:3, 4:6 to 6:4, or about 1:1.

The phosphonic anhydrides of formula II, including mixtures thereof may be prepared by any method known to those of ordinary skill in the art, for example, by reacting the respective phosphonic acid derivatives with acetic anhydride between 30-150° C., and removing acetic acid and acetic anhydride by distillation, according to U.S. Pat. No. 7,473,794 B2, which is incorporated herein by reference in its entirety.

In one embodiment, the phosphonic anhydride is present in an amount of 5-100 mol %, preferably 8-90 mol %, preferably 10-80 mol %, preferably 12-70 mol %, preferably 14-60 mol %, preferably 16-50 mol %, preferably 18-40 mol %, preferably 20-30 mol %, preferably 20-25 mol %, most preferably about 25 mol % relative to a total number of moles of the amine (i.e. if 1.0 mole of amine is used as a starting material, then 25 mol % means 0.25 moles of the phosphonic anhydride is used as the reaction catalyst or promoter). However, the amount of phosphonic anhydride is not limiting and amounts above or below these ranges may be employed and the method may still proceed as intended. For example, in situations where it is desirable to N-formylate an amine containing two amino functionalities (bis-N-formylation), then the amount of phosphonic anhydride may be increased proportionally (e.g. to 10-200 mol % relative to the amine) to account for the two amino groups, and so on, depending on the number of amino groups to be reacted. Likewise, in some situations the amine to be N-formylated is a strong nucleophile (strongly reactive) and the phosphonic anhydride may be employed in amounts less than 5 mol % relative to the moles of amine.

In one embodiment, the phosphonic anhydride may be used in combination with other formylation catalysts or promoters (see below for examples). In one embodiment, the phosphonic anhydride of formula II (or mixtures of phosphonic anhydrides of formula II) is the only catalyst or promoter present that catalyzes/promotes the reaction between the amine and the formamide compound, and no other formylation catalysts or promoters are included as starting materials in the method of N-formylating the amine. In particular, the method is substantially free of one or more of carbodiimides [e.g. dicyclohexylcarbodiimide (DCC), 1-ethyl-3-(3-dimethylaminopropyl)carbodiimide (EDC), N-cyclohexyl-N'-(2-morpholinoethyl)carbodiimide-methyl-p-toluenesulfonate (CMC)], triazolopyridines and salts thereof [e.g. 1-[bis(dimethylamino)methylene]-1H-1,2,3-triazolo[4,5-b]pyridinium 3-oxid hexafluorophosphate (HATU), 7-aza-1-hydroxybenzotriazole (HOAt)], benzotriazoles and salts thereof [e.g. 2-(1H-benzotriazol-1-yl)-1,1,3,3-tetramethyluronium hexafluorophosphate (HBTU), (benzotriazol-1-yloxy)tris(dimethylamino)phosphonium hexafluorophosphate (BOP), benzotriazol-1-yl-oxytripyrrolidinophosphonium hexafluorophosphate (PyBOP), 1-hydroxybenzotriazole (HOBt)], benzotriazin-4-ones [e.g. 3-(diethoxyphosphoryloxy)-1,2,3-benzotriazin-4(3H)-one], carbonyldiimidazole (CDI), phosgene, triphosgene, benzoates (e.g. methyl benzoate), chloroformates [e.g. butyl-, t-butyl-, isobutyl-, isopropyl-, and 4-nitrophenyl chloroformate], cyanuric chlorides including derivatives of cyanuric chlorides [e.g. 2-chloro-4,6-dimethoxy-1,3,5-triazine (CDMT), 4-(4,6-dimethoxy-[1,3,5]triazin-2-yl)-4-methyl-morpholin-4-ium chloride (DMTMM)], 3,3-dichlorocyclopropenes, N-hydroxyphthalimide, aminopyridines (e.g. 4-(dimethylamino)pyridine), solid activated alumina, silica and ion-exchange resins [e.g. KF-alumina, sulfuric acid silica, perchloric acid silica, fluoroboric acid silica, trifluoroacetic acid silica, Amberlite IR-120[H+], sulfonic acid supported on hydroxyapatite (HAp)-encapsulated-γ-$Fe_2O_3$, fluorous silica gel-supported hafnium(IV)bis(perfluorooctanesulfonyl)imide complex (FSG-Hf[N($SO_2C_8F_{17}$)$_2$]$_4$)], alkoxide or carbonate bases [e.g. sodium or potassium methoxide, sodium or potassium ethoxide, kotassium or sodium carbonate], acid catalysts [e.g. melaminetrisulfonic acid (MTSA), sulfuric acid, p-toluene sulfonic acid, methane sulfonic acid, triflic acid], molecular iodine ($I_2$), sodium periodate ($NaIO_4$), thiamine hydrochloride salts, sulfated tungstate catalysts, amidine and guanidine catalysts [e.g. 1,5,7-triazabicyclo[4.4.0]dec-5-ene (TBD)], ionic liquids (e.g. 1-butyl-3-methylimidazolium carbonate), and metals and Lewis acid catalysts (e.g. indium, ZnO, $ZnCl_2$, $FeCl_3$, $AlCl_3$, CuCl, $NiCl_2$, $TiO_2$—P25, $TiO_2$—$SO_4^{2-}$, [Cp*Ir$I_2$]$_2$, gold nanoparticles, Ru—N-heterocyclic carbenes, and triruthenium dodecacarbonyl ($Ru_3(CO)_{12}$), $RuCl_3$, $Co(OAc)_2$].

Amine

The method of the present disclosure involves N-formylation of an amine. Whether the amine or formamide compound is used as the limiting reagent largely depends on the complexity of the amine, the time required for synthesizing the amine, or the financial cost associated with sourcing or synthesizing the amine relative to that of the formamide compound. For example, if the amine is less expensive than the formamide compound, then it may be advantageous to employ the formamide compound as the limiting reagent, with equimolar or excess amine, or if the amine is more expensive than the formamide compound, then it may be advantageous to employ the amine compound as the limiting reagent, with equimolar or excess formamide. Other factors may influence which reagent is used as the limiting reagent, for example, if the amine to be N-formylated is in a gaseous state (e.g. ammonia or methyl amine) it may be difficult to limit the amount of ammonia reacted when in a gaseous state, and so the amine may be bubbled into a reaction mixture in excess. While the method is flexible with respect to which reagent is limiting, in most cases the amine is the limiting reagent. When employed as the limiting reagent, the absolute amount of the amine may be varied widely. Thus in small scale reactions, less than 100 mmol, less than 80 mmol, less than 60 mmol, less than 40 mmol, less than 20 mmol, less than 10 mmol, less than 1 mmol of the amine may be employed. In medium scale reactions, 100 mmol to 1 mol, 200 mmol to 0.8 mol, 500 mmol to 0.6 mol of the amine may be employed. In large scale settings, such as an industrial process, reactions utilizing more than 1 mol, more than 100 mol, more than 1,000 mol of the amine may be employed.

The amine may be in any phase, solid, liquid, or gas at standard temperature and pressure. When the amine is in the form of a solid at room temperature, it is advantageous for the amine to be soluble in an organic solvent. In one embodiment, the amine is in the liquid or gas phase with a boiling point of greater than −10° C., greater than −5° C., greater than 0° C., greater than 10° C., greater than 20° C., greater than 40° C., greater than 60° C., greater than 80° C., greater than 100° C., greater than 140° C., greater than 180° C., greater than 200° C., greater than 250° C., or greater than 300° C. and up to 800° C., up to 600° C., up to 400° C. In a preferred embodiment, an amine is employed in the method herein such that the N-formylated amine product formed is soluble in organic solvent to aid separation from aqueous soluble reaction components (e.g. the phosphonic anhydride, the amine byproduct, etc.).

In one embodiment, the amine is a primary amine. In one embodiment, the amine is of formula (III):

$$R^4\text{—}NH_2 \qquad \text{(III)}$$

wherein $R^4$ is H, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, or an optionally substituted hydrocarbyl, or a salt thereof.

In one embodiment, $R^4$ is an optionally substituted alkyl, an optionally substituted cycloalkyl, an optionally substituted cycloalkylalkyl, or an optionally substituted arylalkyl each containing 1 to 32, 2 to 28, 3 to 24, 4 to 20, 5 to 16, 6 to 14, 7 to 12, 8 to 10 carbon atoms. In one embodiment, $R^4$ is an optionally substituted alkyl and the amine is for example, methyl amine, ethyl amine, 2,2,2-trifluroroethylamine, propylamine, isopropylamine, butyl amine, and the like. In one embodiment, $R^4$ is an optionally substituted cycloalkyl group and the amine is for example, cyclopropylamine, cyclobutylamine, cyclopentylamine, cyclohexylamine, and the like. In one embodiment, R⁴ is an optionally substituted heteroaryl group, and the amine is for example, 3-, or 4-aminopyrazole, aminopyrazine, 3-aminoisoxazole, 2-aminobenzoxazole, 2-aminooxazole, 5-aminoimidazole, 4-amino-1H-pyrazole-3-carboxylate, and the like.

In one embodiment, the amine is an optionally substituted arylamine (aniline functionality) of formula (IV):

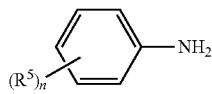

(IV)

wherein each $R^5$ is an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted hydrocarbyl, an optionally substituted alkoxy, an optionally substituted cycloalkyloxy, an optionally substituted aryloxy, an optionally substituted arylalkyloxy, an optionally substituted aroyl, an optionally substituted alkanoyl, an optionally substituted alkanoyloxy, a carboxy, an optionally substituted alkoxycarbonyl, a hydroxyl, a halo, an amino group of the formula —NH₂, —NHR⁶, or —N(R⁶)₂, nitro, cyano, an optionally substituted carbamyl, a thiol, an optionally substituted alkylthio, an optionally substituted arylthio, an optionally substituted arylalkylthio, an optionally substituted alkylsulfonyl, an optionally substituted arylsulfonyl, an optionally substituted arylalkylsulfonyl, and an optionally substituted sulfonamido (e.g. —SO₂NH₂);

each $R^6$ is independently an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted hydrocarbyl, an optionally substituted aroyl, an optionally substituted alkanoyl, an optionally substituted alkoxycarbonyl, an optionally substituted carbamyl, an optionally substituted alkylsulfonyl, an optionally substituted arylsulfonyl, an optionally substituted arylalkylsulfonyl, and an optionally substituted sulfonamido (e.g. —SO₂NH₂); and n is an integer of 0-5, 1-5, 2-5, 3-5, or 4-5.

The method described herein has been found to be general in scope with respect to the amine component and tolerant of a wide range of functional groups, and therefore a broad range of amines can be N-formylated in the method. For example amines containing acid labile groups (e.g. Boc-protecting groups), base labile groups (e.g. esters), as well as amines containing halides, ethers, ketones, and carbamates are all well-tolerated. Furthermore, in the case of arylamines of formula (IV), the method is tolerant of various substitution patterns, and thus substituents that are located ortho, meta, and/or para to the amine being N-formylated are all well-tolerated. In one embodiment, there is no carboxylic acid functionality present during the reacting, for example, none of the reaction components (e.g. the amine, the formamide compound, or the phosphonic anhydride) have carboxylic acid substituents and/or no other reaction components contain a carboxylic acid group, and this includes carboxylate functionality (—COC⁻). Several specific examples of amines suitable in the present method include, but are not limited to

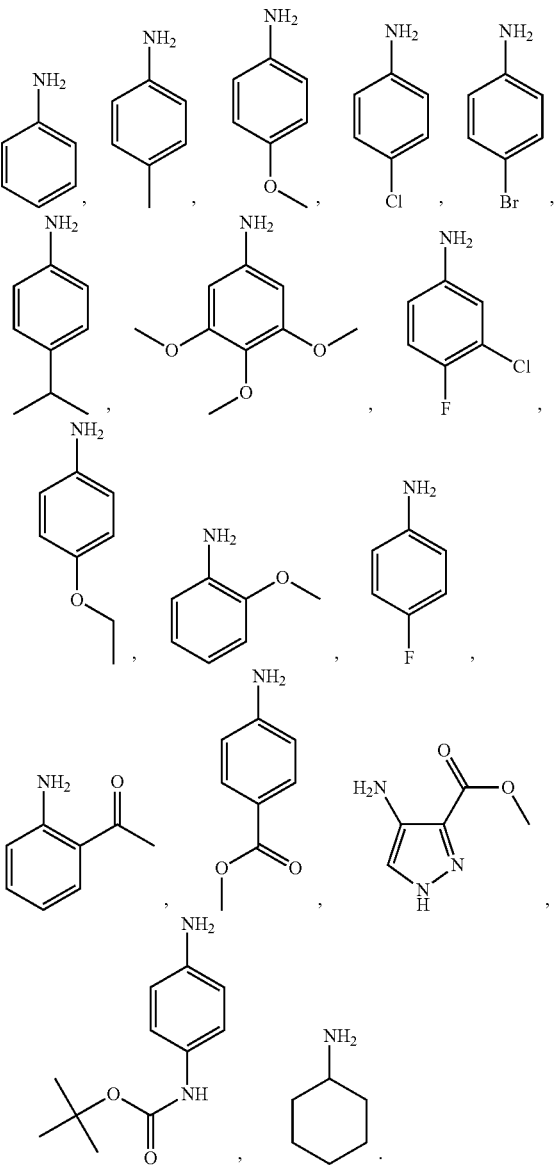

The amine employed in the method herein may be in the form of a salt (quaternary ammonium salt) where the amino group is at least partially protonated and forms an ion pair with a counteranion. For example, amine salts include those derived from inorganic acids such as hydrochloric, hydrobromic, hydrofluoric, hydroiodic, sulfuric, sulfamic, phosphoric, perchloric, hexafluorophosphoric, and nitric acid; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, trifluoromethanesulfonic, ethane disulfonic, oxalic, acetylacetone, hexafluoroacetylacetone, and isethionic, and the like. Generally, such salts can be prepared by reacting the free base form of the amine with a stoichiometric amount of the appropriate acid in water or in an organic solvent, or in a mixture of the two; generally, non-aqueous media like ether, ethyl acetate, ethanol, isopropanol, or acetonitrile are preferred.

Other Reaction Components

In addition to the reaction components previously described (e.g. the formamide compound, the phosphonic anhydride, and the amine), the method may optionally include other reaction components including an organic solvent, a base, a desiccant (e.g. molecular sieves, $MgSO_4$) etc.

In one embodiment, the method, in one or more of its embodiments, further includes at least one organic solvent. Organic solvents include ethers (e.g. diethyl ether, tetrahydrofuran, 1,4-dioxane, tetrahydropyran, t-butyl methyl ether, cyclopentyl methyl ether, di-isopropyl ether), glycol ethers (e.g. 1,2-dimethoxyethane, diglyme, triglyme), alcohols (e.g. methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol), aromatic solvents (e.g. benzene, o-xylene, m-xylene, p-xylene, and mixtures of xylenes, toluene, mesitylene, anisole, 1,2-dimethoxybenzene, $\alpha,\alpha,\alpha$,-trifluoromethylbenzene, fluorobenzene), chlorinated solvents (e.g. chlorobenzene, dichloromethane, 1,2-dichloroethane, 1,1-dichloroethane, chloroform, carbon tetrachloride), ester solvents (e.g. ethyl acetate (EtOAc), propyl acetate), amide solvents (e.g. dimethylacetamide, N-methyl-2-pyrrolidone), urea solvents, ketones (e.g. acetone, butanone), alkane solvents (e.g. pentane, cyclopentane, hexanes, cyclohexane, heptanes, cycloheptane, octanes), acetonitrile, propionitrile, butyronitrile, benzonitrile, dimethyl sulfoxide, ethylene carbonate, propylene carbonate, 1,3-dimethyl-3,4,5,6-tetrahydro-2(1H)-pyrimidinone, nitromethane and mixtures thereof. Amide solvents that include a transferable formyl group (e.g. dimethylformamide) are not considered organic solvents in this disclosure, and are instead considered a formamide compound, even if the formamide compound is used in solvent quantities. In a preferred embodiment, the organic solvent is selected from the group consisting of tetrahydrofuran, acetonitrile, dioxane, toluene, ethylene dichloride, ethyl acetate, and nitromethane. The organic solvent may be used to for dilution purposes, to control the N-formylation reaction rate, to modulate the reaction temperature, to aid transfer of one or more reaction components (e.g. the reacting may be performed by adding a phosphonic anhydride solution comprising the phosphonic anhydride and an organic solvent to a mixture of the amine and the formamide compound), or to aid product purification after the N-formylation reaction is completed. In a preferred embodiment, the reacting is performed by adding a phosphonic anhydride solution comprising the phosphonic anhydride and the organic solvent (e.g. EtOAc) to a mixture of the amine and solvent quantities of the formamide compound. When the organic solvent is present, a volume ratio of the formamide compound to the organic solvent is 20:1 to 1:10, 15:1 to 1:8, 10:1 to 1:6, 5:1 to 1:5, 4:1 to 1:4, 3:1 to 1:3, 2:1 to 1:2, or about 1:1.

In some embodiments, more than one organic solvent may be used, for example a mixture of two or more solvents may be used (e.g. THF and EtOAc). When a mixture of a first organic solvent and a second organic solvent is used, a volume ratio of the first organic solvent to the second organic solvent may be 20:1 to 1:20, 18:2 to 2:18, 16:4 to 4:16, 14:6 to 6:14. In one embodiment, the reacting is performed by adding a phosphonic anhydride solution comprising the phosphonic anhydride and the second organic solvent (e.g. EtOAc) to a mixture of the amine, the formamide compound, and the first organic solvent.

Although the disclosed method is proton neutral, a base may optionally be included in the method, for example, to act as proton shuttle or in cases where a salt of the amine is used, to deprotonate the amine salt. In one embodiment, the base is a tertiary amine having 3-12 carbon atoms, 4-10 carbon atoms, or 5-8 carbon atoms, such as trimethylamine, triethylamine, methyldiethylamine, ethyldimethylamine, triisopropylamine, diisopropylethylamine, dimethylaniline, 1,8-Diazabicyclo[5.4.0]undec-7-ene (DBU), Barton's base, N-methylmorpholine, and the like. In one embodiment, the base is a heteroaromatic amine with 5-, or 6-membered rings containing at least one nitrogen atom within the ring, such as an optionally substituted pyridine (e.g. pyridine), an optionally substituted N-alkylimidazole (e.g. N-methylimidazole), etc. In one embodiment, the base is an inorganic base such as a metal carbonate (e.g. sodium carbonate, potassium carbonate, lithium carbonate), an alkyllithium (e.g. n-butyllithium, t-butyllithium), or a metal hydride (e.g. sodium hydride). In one embodiment, 0-15 molar equivalents, 0.1-10 molar equivalents, 0.5-9 molar equivalents, 1-8 molar equivalents, 2-7 molar equivalents, or 3-6 molar equivalents of the base are used relative to a total number of moles of the amine.

N-formylation Method

The reacting may be performed for 10-30 minutes, 0.5-24 hours, 1-24 hours, 1-12 hours, 2-10 hours, 4-9 hours, or about 8 hours, although shorter or longer reaction durations are also possible. The reaction mixture (i.e. the amine, the formamide compound, the phosphonic anhydride, and any optional reaction components) may be shaken/stirred throughout the duration of the reaction by employing a rotary shaker, a magnetic stirrer, or an overhead stirrer. In another embodiment, the reaction mixture is left to stand (i.e. not stirred). In one embodiment, the reaction mixture is preferably mixed in a centrifugal mixer with a rotational speed of at least 500 rpm, preferably at least 800 rpm, more preferably at least 1,000 rpm. In one embodiment, the reaction mixture is sonicated during the mixing.

Not all components need to be present in their full amounts at the start of the reaction. For example, the amine component, the phosphonic anhydride, and/or any optional reaction components can be metered into the reaction mixture over time or in batches using slow addition techniques known by those of ordinary skill in the art.

The reacting may be performed at a temperature in a range of 25-152° C., preferably 35-110° C., preferably 40-100° C., preferably 45-95° C., preferably 50-90° C., preferably 55-88° C., more preferably 70-85° C., most preferably about 80° C. An external heat source, such as a water bath or an oil bath, an oven, microwave, or a heating mantle, may be employed to heat the reaction mixture. In one embodiment, the external heat source is a thermostatted thermocirculator. In one embodiment, the method does not employ microwave irradiation.

In one embodiment, the reacting is performed in an inert atmosphere provided by an inert gas such as argon, nitrogen, helium, or mixtures thereof. However, owing to the general and mild nature of the disclosed method and the functional group tolerance, the reacting can be performed under a variety of conditions and still function as intended. For example, while the method can be performed under inert atmosphere as described above, or under strict oxygen and/or water free conditions, for example using glove box techniques or Schlenk line techniques, such precautions are not necessary and the method may be performed in air or standard atmospheric conditions where oxygen and moisture are present.

The progress of each reaction may be monitored by methods known to those skilled in the art, such as thin layer chromatography, gas chromatography, nuclear magnetic resonance, infrared spectroscopy, and high pressure liquid chromatography combined with ultraviolet detection or mass spectroscopy. Preferably, thin layer chromatography and gas chromatography combined with mass spectroscopy are used. The percent conversion of the amine (the amount of amine at a given reaction time/amount of amine initially multiplied by 100) can be used as an indicator of reaction progress. Generally, the percent conversion of the amine is greater than 50%, greater than 60%, greater than 70%, greater than 80%, greater than 90%, greater than 95%, greater than 99% after a reaction time of 3-10 hours, or 4-9 hours, or about 8 hours.

The N-formylated amine product can be recovered by isolation/purification procedures known to those of ordinary skill in the art, such as crystallization or recrystallization from an appropriate solvent, filtration through a celite containing cartridge, aqueous work-up, extraction with organic solvents, distillation, precipitation, column chromatography, and medium pressure liquid chromatography (MPLC) or high pressure liquid chromatography (HPLC) on normal phase or reversed phase, or a combination of these techniques.

In one embodiment, when the method is deemed complete, it may be advantageous to distill off a portion of the formamide compound remaining in the medium after the reaction, if the boiling point of the formamide compound used is lower than the N-formylated amine product and if the formamide compound was deployed in a molar excess to the amine starting material.

In one embodiment, the N-formylated amine is isolated by precipitation. To do this, water is added to the reaction medium, preferably between about 1 to 10 parts by weight of water per part by weight of the formamide compound or the organic solvent, whichever is greater. The N-formylated amine may then precipitate out of solution and be collected through filtration. This precipitation procedure can be modified to include an acid, in particular an inorganic acid, for example hydrochloric or sulfuric acid, so that there is a pH of approximately 0 to 4, preferably of approximately 2 to 3, at the end of the precipitation. For example, the acid may be added to the water needed for the precipitation to achieve an acidic pH, preferably a pH of approximately 2 to 3, and then the reaction medium and the acidified water are mixed. Alternatively, the reaction medium can be first quenched by the addition of the appropriate amount of water, followed by acidification with the acid to achieve the appropriate pH.

Preferably, the method involves isolating the N-formylated amine by extraction with organic solvents followed by purification (e.g. column chromatography). To do this, water or an aqueous solution (e.g. ammonium chloride solution, a dilute HCl solution, citric acid solution, etc.) is added to the reaction medium, preferably between about 1 to 10 parts by weight of water or aqueous solution per part by weight of the formamide compound or the organic solvent, whichever is greater, and the N-formylated amine is extracted using a suitable organic solvent, such as diethylether, ethyl acetate, dichloromethane, etc. The extraction may be performed once or a plurality of times depending on the extraction efficiency of the solvent and the hydrophobicity of the N-formylated amine. The combined organic phase may optionally be neutralized or washed with an aqueous bicarbonate solution (e.g. saturated sodium bicarbonate), brine, or both, dried over a desiccant (e.g. $Na_2SO_4$ or $MgSO_4$), and concentrated under heat and/or reduced pressure. The isolated N-formylated amine may then be purified by recrystallization, column chromatography (e.g. elusion through silica gel with organic solvents), distillation, and/or lyophilization techniques known to those of ordinary skill.

In one embodiment, the isolated yield of the N-formylated amine is at least 80%, preferably at least 85%, more preferably at least 90%, more preferably at least 95%, more preferably at least 99%, based on the initial number of moles of the amine. In one embodiment, the formamide compound is present in an amount of at least 10 mole equivalents, the phosphonic anhydride is present in an amount of 10-30 mol %, preferably 20-25 mol %, and the N-formylated amine is formed in an isolated yield of at least 85%, each based on a total number of moles of the amine. The purity of the N-formylated amine can be determined by those of ordinary skill, including techniques such as thin layer chromatography, gas chromatography, nuclear magnetic resonance, infrared spectroscopy, mass measurements, mass spectroscopy, X-ray diffraction, and high pressure liquid chromatography combined with ultraviolet detection or mass spectroscopy.

In cases where the N-formylated amine produced is not the desired final product, but is instead used as an intermediate or a protected intermediate, following use of the N-formylated product (e.g., in dipeptide synthesis), the N-formyl group can be returned to the amine form by mild hydrolysis if desired, as known to those of ordinary skill in the art.

Figure 2:
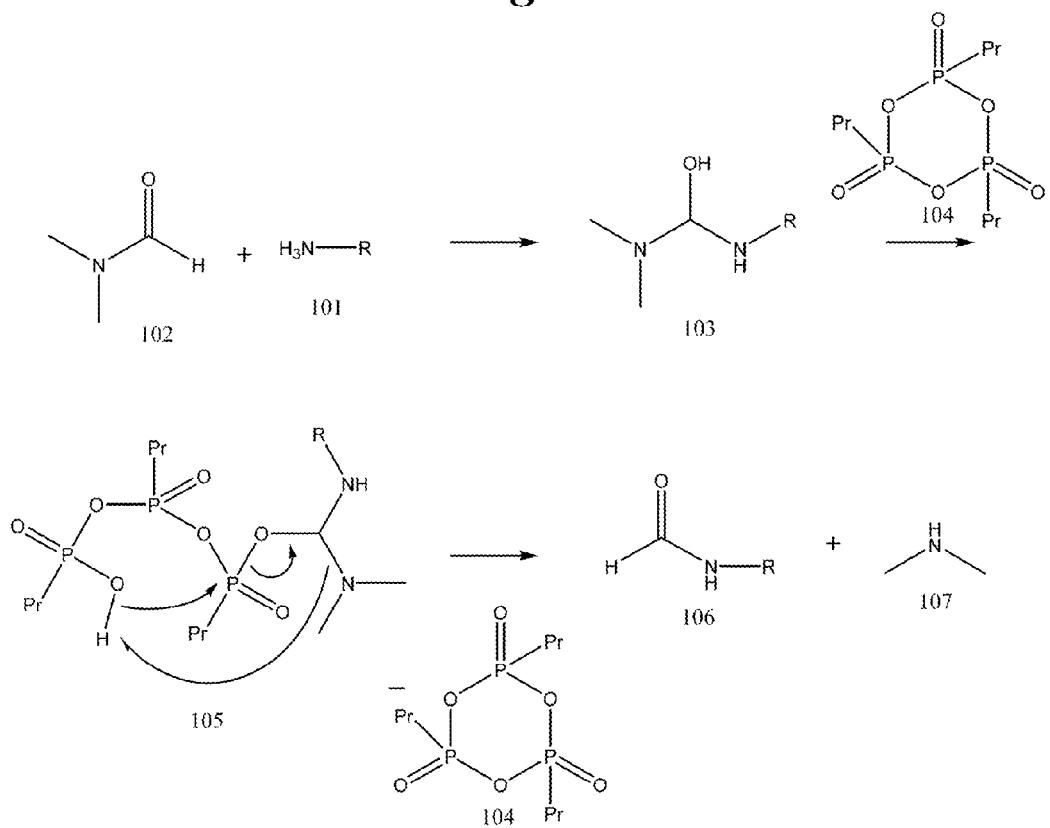
FIG. 2 is a general reaction mechanism for the N-formylation reaction.

The reactivity of the phosphonic anhydride, in particular propylphosphonic anhydride, T3P®, for promoting/catalysing the N-formylation reaction herein between the amine and the formamide compound is surprising. Typically, when such reagents (e.g. T3P®) are employed in amine-carboxylic acid coupling reactions to form amides, the carboxylic acid or carboxylate group first acts as a nucleophile and ring opens the cyclic phosphonic anhydride to form an activated linear acyl phosphonate. The activated carboxylate group (i.e. the activated linear acyl phosphonate) is an electrophile at the carboxylate carbonyl center and is attacked by the amine resulting in amide bond formation and a linear phosphonate byproduct being ejected as a leaving group. Because for each reaction cycle in such amide coupling reactions the cyclic phosphonic anhydride is destroyed (i.e. forms linear phosphonate byproducts), the phosphonic anhydride must be used in stoichiometric quantities. The reactivity and reaction mechanism of the method disclosed herein differs greatly from these well-known coupling reactions and is quite unexpected (FIG. 2). In the present method, the amine 101 and the formamide compound 102 (e.g. DMF) may first react reversibly to form a geminal diaminoalcohol 103. The geminal diamino alcohol 103 may then react with the cyclic phosphonic anhydride 104 in a ring-opening event to form phosphonate 105, which can then undergo rearrangement upon ring re-closure to transfer the formyl group to the amine starting material, thereby forming the N-formylated amine 106, an amine byproduct 107 and reforming the cyclic phosphonic anhydride 104. The reactivity of the cyclic phosphonic anhydride in the method herein is therefore unexpected since it can be used in catalytic amounts (i.e. it is regenerated during the reaction), and unlike the amine/carboxylic acid coupling reaction, the ring-opened phosphonate undergoes rearrangement rather than acting as a leaving group.

Having generally described this disclosure, a further understanding can be obtained by reference to certain specific examples which are provided herein for purposes of illustration only and are not intended to be limiting unless otherwise specified.

Example 1

Initial Experiments

Initially the experiment was carried out with neat aniline (1.0 eq) in DMF (10V) at 80° C. without propyl phosphonic anhydride. 5-6% conversions of aniline to N-formylated product after 24 h were observed. Whereas the addition of propyl phosphonic anhydride (1.0 eq, 50% solution in EtOAc) enhanced the rate of the reaction and showed 99% conversion in 8 h. Lesser quantities of propyl phosphonic anhydride e.g. 25 mol % of propyl phosphonic anhydride was deemed sufficient for the complete conversion of the substrate (Table 2, entry 1). Next the reaction was screened for the solvents (Table 1).

TABLE 1

Screening for solvents and T3P with aniline starting material

| Entry | Solvent (10 V) | T3P (mol %.) | DMF | Temp. (° C.) | % Conversion after 8 h. |
|---|---|---|---|---|---|
| 1 | THF | 25 | 1.0 eq | 70 | 0 |
| 2 | MeCN | 25 | 1.0 eq | 70 | 0 |
| 3 | Dioxane | 25 | 1.0 eq | 100 | 0 |
| 4 | Toluene | 25 | 1.0 eq | 100 | 0 |
| 5 | EDC | 25 | 1.0 eq | 70 | 0 |
| 6 | MeNO2 | 25 | 1.0 eq | 70 | 0 |
| 7 | THF | 25 | 10 (V) | 80 | 55 |
| 8 | — | 25 | 10 (V) | 80 | 99 |
| 9 | — | 20 | 10 (V) | 80 | 88 |

Example 2

General Procedure

To a solution of amine (0.01 mol) in DMF (10 mL) was added T3P (25 mol %, 50% soln in EtOAc) and the resulting reaction mixture was stirred at 80° C. for 5-9 h under nitrogen atmosphere. When the reaction was completed as confirmed by TLC, the reaction mass was diluted with water (20 mL). The product was extracted with ethyl acetate (2×20 mL) and the combined organic phase was washed with saturated $NaHCO_3$ solution (1×10 mL) and brine. The organic phase was dried over anhydrous $Na_2SO_4$. The solvent was removed under reduced pressure, the residue obtained was subjected to column chromatography using 60-120 silica mesh and EtOAc/Hexane as eluent to afford pure N-formyl amine. The structure of the product was confirmed by spectral (FT-IR, 1H NMR and MS) and analytical data.

Example 3

Reaction Scope

With the most favorable reaction conditions (Table 1, entry 8) in hand the scope and generality of this reaction were explored. Thus, various primary amines were treated with T3P under the standard reaction conditions (Table 1, entry 8) to obtain corresponding N-formylated products. As summarized in Table 2, the reaction is applicable also to heteroaromatic (Table 2, entry 14) and aliphatic (Table 2, entry 16) primary amines to afford the corresponding N-formylated products in good yield. It is noteworthy that the reaction tolerated an acid sensitive functional group to provide the N-formylated products in good yields (Table 2, entries 14-17). In most cases, the products were isolated after quenching reaction mass to water, extraction with ethyl acetate, concentration and finally purified by column chromatography.

In the product we have observed cis as the major isomer (~70%). To check the feasibility of reaction in scale up batches reactions with 3-Chloro, 4-fluoro aniline (50 g, 0.343 mol) in DMF (500 ml) followed by addition of T3P (54.64 ml, 25 mol %, 50% solution in EtOAc)) then heating the reaction mixture to 80° C. for 5.5 h were performed. After the work up the isolated yield (58.3 g, 97.9%) was consistent with the small batch.

A novel and highly efficient method for the conversion of primary amines to N-formyl amines where T3P can be used as an excellent catalyst has been developed. Unlike other methods, the use of catalytic amount of T3P (25 mol % or 0.25 eq) is economical. The method seems to be convenient for large scale preparations due to the ease of isolation of products in good purity by simple work-up and can be used as a valid substitute for other methods, thus avoiding the use of expensive and more toxic reagents. The method has shown high functional group tolerance in the case of acid sensitive moieties.

TABLE 2

T3P mediated conversion of primary amines to formamides.

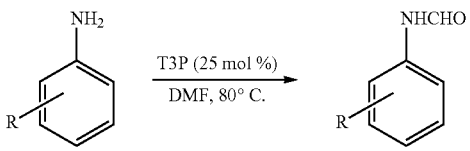

| Entry | Amine | Product | Time(h) | Isolated yield[a] (%) |
|---|---|---|---|---|
| 1 | $NH_2$ | NHCHO | 8 | 94 |

TABLE 2-continued
T3P mediated conversion of primary amines to formamides.
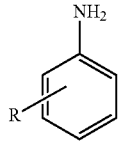
| Entry | Amine | Product | Time(h) | Isolated yield[a] (%) |
|---|---|---|---|---|
| 2 | 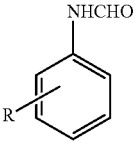 | 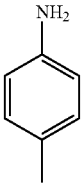 | 7 | 96 |
| 3 | 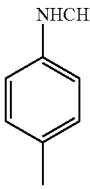 | 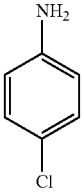 | 7 | 94.5 |
| 4 | 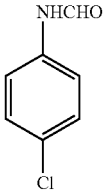 | 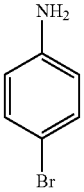 | 8 | 96 |
| 5 | 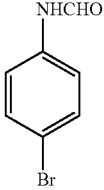 | 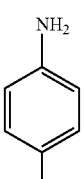 | 9 | 97 |
| 6 | 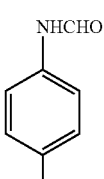 | 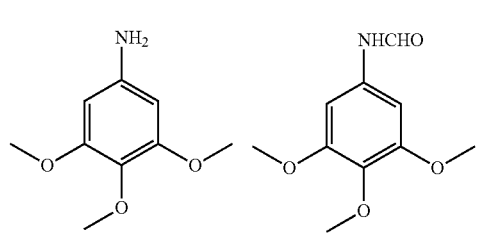 | 6.5 | 94 |
| 7 |  | | 8.5 | 88 |

TABLE 2-continued

T3P mediated conversion of primary amines to formamides.

R—C₆H₄—NH₂ —(T3P (25 mol %), DMF, 80° C.)→ R—C₆H₄—NHCHO

| Entry | Amine | Product | Time(h) | Isolated yield[a] (%) |
|---|---|---|---|---|
| 8 | 4-F, 3-Cl aniline | 4-F, 3-Cl formanilide | 5.5 | 98 |
| 9 | 4-ethoxyaniline | 4-ethoxyformanilide | 7.5 | 95 |
| 10 | 2-methoxyaniline | 2-methoxyformanilide | 8 | 92 |
| 11 | 4-fluoroaniline | 4-fluoroformanilide | 7 | 96 |
| 12 | 2'-aminoacetophenone | 2'-formamidoacetophenone | 10 | 85 |
| 13 | methyl 4-aminobenzoate | methyl 4-formamidobenzoate | 9 | 97 |

TABLE 2-continued

T3P mediated conversion of primary amines to formamides.

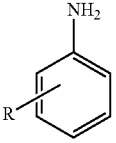

| Entry | Amine | Product | Time(h) | Isolated yield[a] (%) |
|---|---|---|---|---|
| 14 | 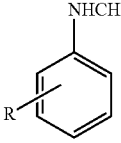 | 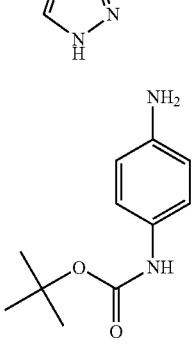 | 8 | 96 |
| 15 | 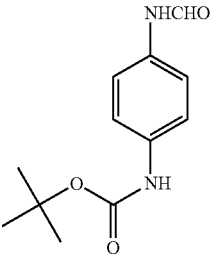 | 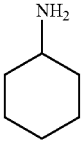 | 7 | 97.5 |
| 16 | NH₂-cyclohexyl | NHCHO-cyclohexyl | 9 | 93 |

[a] Yields are of pure isolated products characterized by their physical constants, spectral (FT-IR, ¹H NMR and MS) and analytical data.

Example 4

N-Phenylformamide

To a solution of aniline (2 g, 21.4 mmol) in dimethyl formamide (20 ml) was added T3P (2.49 ml, 4.29 mmol, 50% solution in EtOAc) and the resulting reaction mixture was stirred at 80° C. for 8 h under nitrogen atmosphere (the reaction was monitored by TLC and its completion was confirmed by the same). The reaction mass was diluted with water (40 ml) and extracted with ethyl acetate (2×40 ml), the combined organic layer was washed with saturated NaHCO₃ solution (1×40 ml) and brine solution (1×40 ml). The organic layer was dried over anhydrous Na₂SO₄. The solvent was removed under reduced pressure; the residue obtained was purified by column chromatography using 60-120 silica mesh and eluents: initially with 100% pet ether and finally with 10% ethyl acetate in pet ether to afford pure N-Phenylformamide and product was confirmed by ¹H NMR. HPLC: 99%
Yield (%): 90

Example 5

Methyl 4-(formylamino)-1H-pyrazole-3-carboxylate

To a solution of Methyl 4-amino-1H-pyrazole-3-carboxylate (0.8 g, 5.66 mmol) in dimethyl formamide (8.0 ml) was added T3P (0.658 ml, 1.113 mmol, 50% solution in EtOAc) and the resulting reaction mixture was stirred at 80° C. for 7 h under nitrogen atmosphere (the reaction was monitored by TLC and its completion was confirmed by the same). The reaction mass was diluted with water (16 ml) and extracted with ethyl acetate (2×16 ml), the combined organic layer was washed with saturated NaHCO₃ solution (1×16 ml) and brine solution (1×16 ml). The organic layer was dried over anhydrous Na₂SO₄. The solvent was removed under reduced pressure; the residue obtained was purified by column chromatography using 60-120 silica mesh and eluents: initially with 100% pet ether and finally with 15% ethyl acetate in pet ether to afford pure Methyl 4-(formylamino)-1H-pyrazole-3-carboxylate and product was confirmed by ¹H NMR. HPLC: 98%
Yield (%): 92

Example 6 tert-Butyl [4-(formylamino)phenyl]carbamate

To a solution of tert-butyl (4-aminophenyl)carbamate (1 g, 4.8 mmol) in dimethyl formamide (10 ml) was added T3P (0.55 ml, 0.96 mmol, 50% solution in EtOAc) and the resulting reaction mixture was stirred at 80° C. for 7 h under nitrogen atmosphere (the reaction was monitored by TLC and its completion was confirmed by the same). The reaction mass was diluted with water (20 ml) and extracted with ethyl acetate (2×20 ml), the combined organic layer was washed with saturated NaHCO₃ solution (1×20 ml) and brine solution (1×20 ml). The organic layer was dried over anhydrous Na$_2$SO$_4$ and solvent was removed under reduced pressure to afford pure tert-Butyl [4-(formylamino)phenyl]carbamate and product was confirmed by $^1$H NMR. HPLC: 95%
Yield (%): 95.5

Example 7

N-(3, 4, 5-Trimethoxyphenyl)formamide

To a solution of 3, 4, 5-Trimethoxyaniline (1 g, 5.45 mmol) in dimethyl formamide (10 ml) was added T3P (0.63 ml, 1.09 mmol, 50% solution in EtOAc) and the resulting reaction mixture was stirred at 80° C. for 8 h under nitrogen atmosphere (the reaction was monitored by TLC and its completion was confirmed by the same). The reaction mass was diluted with water (20 ml) and extracted with ethyl acetate (2×20 ml), the combined organic layer was washed with saturated NaHCO$_3$ solution (1×20 ml) and brine solution (1×20 ml). The organic layer was dried over anhydrous Na$_2$SO$_4$. The solvent was removed under reduced pressure; the residue obtained was purified by column chromatography using 60-120 silica mesh and eluents: initially with 100% pet ether and finally with 18% ethyl acetate in pet ether to afford pure N-(3, 4, 5-Trimethoxyphenyl)formamide and product was confirmed by $^1$H NMR. HPLC: 93%
Yield (%): 88

Example 8

N-(3-Chloro-4-fluorophenyl)formamide

To a solution of 3-Chloro-4-fluoroaniline (1 g, 6.87 mmol) in dimethyl formamide (10 ml) was added T3P (0.79 ml, 1.37 mmol, 50% solution in EtOAc) and the resulting reaction mixture was stirred at 80° C. for 6 h under nitrogen atmosphere (the reaction was monitored by TLC and its completion was confirmed by the same). The reaction mass was diluted with water (20 ml) and extracted with ethyl acetate (2×20 ml), the combined organic layer was washed with saturated NaHCO$_3$ solution (1×20 ml) and brine solution (1×20 ml). The organic layer was dried over anhydrous Na$_2$SO$_4$ and solvent was removed under reduced pressure to afford pure N-(3-Chloro-4-fluorophenyl)formamide and product was confirmed by $^1$H NMR. HPLC: 93%
Yield (%): 98

Example 9

N-(2-Acetylphenyl)formamide

To a solution of 1-(2-Aminophenyl)ethanone (1 g, 7.39 mmol) in dimethyl formamide (10 ml) was added T3P (0.86 ml, 1.47 mmol, 50% solution in EtOAc) and the resulting reaction mixture was stirred at 80° C. for 10 h under nitrogen atmosphere (the reaction was monitored by TLC and its completion was confirmed by the same). The reaction mass was diluted with water (20 ml) and extracted with ethyl acetate (2×20 ml), the combined organic layer was washed with saturated NaHCO$_3$ solution (1×20 ml) and brine solution (1×20 ml). The organic layer was dried over anhydrous Na$_2$SO$_4$. The solvent was removed under reduced pressure; the residue obtained was purified by column chromatography using 60-120 silica mesh and eluents: initially with 100% pet ether and finally with 12% ethyl acetate in pet ether to afford pure N-(2-Acetylphenyl)formamide and product was confirmed by $^1$H NMR. HPLC: 99%
Yield (%): 85

Example 10

Methyl 4-(formylamino)benzoate

To a solution of Methyl 4-aminobenzoate (1 g, 6.61 mmol) in dimethyl formamide (10 ml) was added T3P (0.76 ml, 1.32 mmol, 50% solution in EtOAc) and the resulting reaction mixture was stirred at 80° C. for 6.5 h under nitrogen atmosphere (the reaction was monitored by TLC and its completion was confirmed by the same). The reaction mass was diluted with water (20 ml) and extracted with ethyl acetate (2×20 ml), the combined organic layer was washed with saturated NaHCO$_3$ solution (1×20 ml) and brine solution (1×20 ml). The organic layer was dried over anhydrous Na$_2$SO$_4$. The organic layer was dried over anhydrous Na$_2$SO$_4$ and solvent was removed under reduced pressure to afford pure Methyl 4-(formylamino)benzoate and product was confirmed by $^1$H NMR. HPLC: 99%
Yield (%): 97

Example 11

N-(4-Methoxyphenyl)formamide

To a solution of 4-Methoxyaniline (2 g, 16.2 mmol) in dimethyl formamide (20 ml) was added T3P (1.88 ml, 3.24 mmol, 50% solution in EtOAc) and the resulting reaction mixture was stirred at 80° C. for 7 h under nitrogen atmosphere (the reaction was monitored by TLC and its completion was confirmed by the same). The reaction mass was diluted with water (40 ml) and extracted with ethyl acetate (2×40 ml), the combined organic layer was washed with saturated NaHCO$_3$ solution (1×40 ml) and brine solution (1×40 ml). The organic layer was dried over anhydrous Na$_2$SO$_4$. The solvent was removed under reduced pressure; the residue obtained was purified by column chromatography using 60-120 silica mesh and eluents: initially with 100% pet ether and finally with 10% ethyl acetate in pet ether to afford pure N-(4-Methoxyphenyl)formamide and product was confirmed by $^1$H NMR. HPLC: 98%
Yield (%): 94.5

Example 12

N-(4-Methylphenyl)formamide

To a solution of 4-Methylaniline (2 g, 18.6 mmol) in dimethyl formamide (20 ml) was added T3P (2.17 ml, 3.73 mmol, 50% solution in EtOAc) and the resulting reaction mixture was stirred at 80° C. for 6.5 h under nitrogen atmosphere (the reaction was monitored by TLC and its completion was confirmed by the same). The reaction mass was diluted with water (40 ml) and extracted with ethyl acetate (2×40 ml), the combined organic layer was washed with saturated NaHCO$_3$ solution (1×40 ml) and brine solution (1×40 ml). The organic layer was dried over anhydrous Na$_2$SO$_4$. The solvent was removed under reduced pressure; the residue obtained was purified by column chromatography using 60-120 silica mesh and eluents: initially with 100% pet ether and finally with 8% ethyl acetate in pet ether to afford pure N-(4-Methylphenyl)formamide and product was confirmed by $^1$H NMR. HPLC: 91%
Yield (%): 96

Example 13

N-(4-Chlorophenyl)formamide

To a solution of 4-Chloroaniline (1.5 g, 11.7 mmol) in dimethyl formamide (15 ml) was added T3P (1.36 ml, 2.35 mmol, 50% solution in EtOAc) and the resulting reaction mixture was stirred at 80° C. for 8 h under nitrogen atmosphere (the reaction was monitored by TLC and its completion was confirmed by the same). The reaction mass was diluted with water (30 ml) and extracted with ethyl acetate (2×30 ml), the combined organic layer was washed with saturated NaHCO$_3$ solution (1×30 ml) and brine solution (1×30 ml). The organic layer was dried over anhydrous Na$_2$SO$_4$. The solvent was removed under reduced pressure; the residue obtained was purified by column chromatography using 60-120 silica mesh and eluents: initially with 100% pet ether and finally with 9% ethyl acetate in pet ether to afford pure N-(4-Chlorophenyl)formamide and product was confirmed by $^1$H NMR. HPLC: 92%
Yield (%): 96

Example 14

N-(4-Bromophenyl)formamide

To a solution of 4-Bromoaniline (1 g, 5.81 mmol) in dimethyl formamide (10 ml) was added T3P (0.67 ml, 1.16 mmol, 50% solution in EtOAc) and the resulting reaction mixture was stirred at 80° C. for 6 h under nitrogen atmosphere (the reaction was monitored by TLC and its completion was confirmed by the same). The reaction mass was diluted with water (20 ml) and extracted with ethyl acetate (2×20 ml), the combined organic layer was washed with saturated NaHCO$_3$ solution (1×20 ml) and brine solution (1×20 ml). The organic layer was dried over anhydrous Na$_2$SO$_4$. The solvent was removed under reduced pressure; the residue obtained was purified by column chromatography using 60-120 silica mesh and eluents: initially with 100% pet ether and finally with 10% ethyl acetate in pet ether to afford pure N-(4-Bromophenyl)formamide and product was confirmed by $^1$H NMR. HPLC: 98%
Yield (%): 94

Example 15

N-[4-(Propan-2-yl)phenyl]formamide

To a solution of 4-(Propan-2-yl)aniline (1 g, 7.39 mmol) in dimethyl formamide (10 ml) was added T3P (0.86 ml, 1.47 mmol, 50% solution in EtOAc) and the resulting reaction mixture was stirred at 80° C. for 9 h under nitrogen atmosphere (the reaction was monitored by TLC and its completion was also confirmed by the same). The reaction mass was diluted with water (20 ml) and extracted with ethyl acetate (2×20 ml), the combined organic layer was washed with saturated NaHCO$_3$ solution (1×20 ml) and brine solution (1×20 ml). The organic layer was dried over anhydrous Na$_2$SO$_4$. The solvent was removed under reduced pressure; the residue obtained was purified by column chromatography using 60-120 silica mesh and eluents: initially with 100% pet ether and finally with 12% ethyl acetate in pet ether to afford pure N-[4-(Propan-2-yl)phenyl]formamide and product was confirmed by $^1$H NMR. HPLC: 93%
Yield (%): 88

Example 16

N-(4-Ethoxyphenyl)formamide

To a solution of 4-Ethoxyaniline (1 g, 7.29 mmol) in dimethyl formamide (10 ml) was added T3P (0.84 ml, 1.45 mmol, 50% solution in EtOAc) and the resulting reaction mixture was stirred at 80° C. for 10 h under nitrogen atmosphere (the reaction was monitored by TLC and its completion was confirmed by the same). The reaction mass was diluted with water (20 ml) and extracted with ethyl acetate (2×20 ml), the combined organic layer was washed with saturated NaHCO$_3$ solution (1×20 ml) and brine solution (1×20 ml). The organic layer was dried over anhydrous Na$_2$SO$_4$. The solvent was removed under reduced pressure; the residue obtained was purified by column chromatography using 60-120 silica mesh and eluents: initially with 100% pet ether and finally with 14% ethyl acetate in pet ether to afford pure N-(4-Ethoxyphenyl)formamide and product was confirmed by $^1$H NMR. HPLC: 95%
Yield (%): 90

Example 17

N-(4-Iodophenyl)formamide

To a solution of 4-Iodoaniline (1.5 g, 6.84 mmol) in dimethyl formamide (15 ml) was added T3P (0.79 ml, 1.36 mmol, 50% solution in EtOAc) and the resulting reaction mixture was stirred at 80° C. for 6 h under nitrogen atmosphere (the reaction was monitored by TLC and its completion was confirmed by the same). The reaction mass was diluted with water (30 ml) and extracted with ethyl acetate (2×30 ml), the combined organic layer was washed with saturated NaHCO$_3$ solution (1×30 ml) and brine solution (1×30 ml). The organic layer was dried over anhydrous Na$_2$SO$_4$. The organic layer was dried over anhydrous Na$_2$SO$_4$ and solvent was removed under reduced pressure to afford pure N-(4-Iodophenyl)formamide and product was confirmed by $^1$H NMR. HPLC: 95%
Yield (%): 95

Example 18

N-(4-Fluorophenyl)formamide

To a solution of 4-Fluoroaniline (1 g, 9.0 mmol) in dimethyl formamide (10 ml) was added T3P (1.04 ml, 1.8 mmol, 50% solution in EtOAc) and the resulting reaction mixture was stirred at 80° C. for 7.5 h under nitrogen atmosphere (the reaction was monitored by TLC and its completion was confirmed by the same). The reaction mass was diluted with water (20 ml) and extracted with ethyl acetate (2×20 ml), the combined organic layer was washed with saturated NaHCO$_3$ solution (1×20 ml) and brine solution (1×20 ml). The organic layer was dried over anhydrous Na$_2$SO$_4$. The solvent was removed under reduced pressure; the residue obtained was purified by column chromatography using 60-120 silica mesh and eluents: initially with 100% pet ether and finally with 12% ethyl acetate in pet ether to afford pure N-(4-Fluorophenyl)formamide and product was confirmed by $^1$H NMR. HPLC: 99% Yield (%): 96

Example 19

Mechanism

Initial attack of the amine on the carbonyl carbon of the formamide compound, and prior to imine formation, the hydroxyl group will attack T3P to produce the intermediate 105. Finally intermediate 105, which is not stable, converts into the N-formylated amine product and regenerates T3P.

The invention claimed is:

1. A method for N-formylating an amine, comprising:
reacting the amine and a formamide compound in the presence of a phosphonic anhydride to form an N-formylated amine,
wherein the formamide compound is of formula (I), the phosphonic anhydride is of formula (II), and the amine is of formula (III):

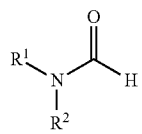
(I)

wherein $R^1$ and $R^2$ are independently H, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl or an optionally substituted hydrocarbyl, with $R^1$ and $R^2$ also being able to form, together with the nitrogen atom to which they are bound, a saturated or unsaturated 3- to 6-membered heterocyclic ring;

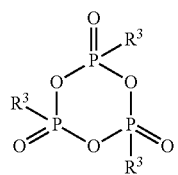
(II)

wherein each $R^3$ is independently an optionally substituted alkyl, an optionally substituted cycloalkyl, an optionally substituted cycloalkylalkyl, an optionally substituted arylalkyl, an optionally substituted aryl, or an optionally substituted hydrocarbyl;

$$R^4-NH_2 \quad (III)$$

wherein $R^4$ is H, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, or an optionally substituted hydrocarbyl.

2. The method of claim 1, wherein $R^1$ and $R^2$ are independently an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, or an optionally substituted hydrocarbyl.

3. The method of claim 1, wherein $R^1$ and $R^2$ are independently an optionally substituted alkyl.

4. The method of claim 1, wherein $R^1$ and $R^2$ are each methyl.

5. The method of claim 1, wherein the formamide compound is present in an amount of at least 5 mole equivalents relative to a total number of moles of the amine.

6. The method of claim 1, wherein each $R^3$ is the same.

7. The method of claim 6, wherein $R^3$ is an optionally substituted alkyl.

8. The method of claim 6, wherein $R^3$ is propyl.

9. The method of claim 1, wherein the phosphonic anhydride is present in an amount of 5-100 mol % relative to a total number of moles of the amine.

10. The method of claim 1, wherein the phosphonic anhydride is present in an amount of 10-30 mol % relative to a number of moles of the amine.

11. The method of claim 1, wherein the amine is an optionally substituted arylamine of formula (IV):

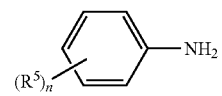
(IV)

wherein each $R^5$ is an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted hydrocarbyl, an optionally substituted alkoxy, an optionally substituted cycloalkyloxy, an optionally substituted aryloxy, an optionally substituted arylalkyloxy, an optionally substituted aroyl, an optionally substituted alkanoyl, an optionally substituted alkanoyloxy, a carboxy, an optionally substituted alkoxycarbonyl, a hydroxyl, a halo, an amino group of the formula $-NH_2$, $-NHR^6$, or $-N(R^6)_2$, nitro, cyano, an optionally substituted carbamyl, a thiol, an optionally substituted alkylthio, an optionally substituted arylthio, an optionally substituted arylalkylthio, an optionally substituted alkylsulfonyl, an optionally substituted arylsulfonyl, an optionally substituted arylalkylsulfonyl, and an optionally substituted sulfonamido (e.g. $-SO_2NH_2$);

each $R^6$ is independently an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted hydrocarbyl, an optionally substituted aroyl, an optionally substituted alkanoyl, an optionally substituted alkoxycarbonyl, an optionally substituted carbamyl, an optionally substituted alkylsulfonyl, an optionally substituted arylsulfonyl, an optionally substituted arylalkylsulfonyl, and an optionally substituted sulfonamido (e.g. —SO$_2$NH$_2$); and n is an integer of 0-5.

12. The method of claim 1, further comprising at least one organic solvent selected from the group consisting of tetrahydrofuran, acetonitrile, dioxane, toluene, ethylene dichloride, ethyl acetate, and nitromethane.

13. The method of claim 1, wherein the reacting is performed for 1-24 hours at a temperature of 45-100° C.

14. The method of claim 1, wherein the formamide compound is present in an amount of at least 10 mole equivalents, the phosphonic anhydride is present in an amount of 10-30 mol %, and the N-formylated amine is formed in an isolated yield of at least 80%, each based on a total number of moles of the amine.

15. The method of claim 1, wherein the reacting is performed by adding a phosphonic anhydride solution comprising the phosphonic anhydride and an organic solvent to a mixture of the amine and the formamide compound.

16. The method of claim 1, wherein the phosphonic anhydride is the only compound present that catalyzes the reaction between the amine and the formamide compound.

17. The method of claim 1, wherein the formamide compound is the only formylating agent present.

* * * * *